United States Patent
Miser

(10) Patent No.: US 6,679,874 B2
(45) Date of Patent: Jan. 20, 2004

(54) RATCHETING MECHANISM FOR ENDOSCOPIC INSTRUMENTS

(75) Inventor: John D. Miser, Apex, NC (US)

(73) Assignee: Weck Closure Systems, Inc., Research Triangle Park, NC (US)

( * ) Notice: Subject to any disclaimer, the term of this patent is extended or adjusted under 35 U.S.C. 154(b) by 266 days.

(21) Appl. No.: 09/972,170

(22) Filed: Oct. 5, 2001

(65) Prior Publication Data

US 2003/0069565 A1 Apr. 10, 2003

(51) Int. Cl.[7] .............................................. A61B 17/00
(52) U.S. Cl. ............................ 606/1; 600/137; 606/46; 606/205
(58) Field of Search .......................... 606/1, 46, 51, 606/52, 167, 170, 205; 600/137

(56) References Cited

U.S. PATENT DOCUMENTS

| | | | |
|---|---|---|---|
| 4,207,873 A | * 6/1980 | Kruy | 600/146 |
| 5,174,300 A | * 12/1992 | Bales et al. | 600/564 |
| 5,556,416 A | 9/1996 | Clark et al. | |
| 5,827,323 A | 10/1998 | Klieman et al. | |
| 5,836,960 A | 11/1998 | Kolesa et al. | |
| 5,893,835 A | * 4/1999 | Witt et al. | 601/2 |
| 6,068,647 A | 5/2000 | Witt et al. | |

* cited by examiner

Primary Examiner—Michael Peffley
(74) Attorney, Agent, or Firm—Burns, Doane, Swecker & Mathis, L.L.P.

(57) ABSTRACT

A incremental rotational displacement mechanism is provided. The mechanism includes a circular detent housing having a plurality of detents arranged along the circumference of the detent housing. A detent ring is positioned coplanar to and within the circumference of the detent housing. At least a portion of the at least one detent arm engages at least a portion of the detent housing. A handle may engage the detent ring, so that a force applied to the handle causes the detent ring to rotate with respect to the circular detent housing. The mechanism is suitable for a variety of applications, including endoscopic instruments.

14 Claims, 7 Drawing Sheets

RATCHETING MECHANISM FOR ENDOSCOPIC INSTRUMENTS

BACKGROUND

This invention generally relates to endoscopic instruments. More particularly, the present invention provides a ratcheting mechanism to rotationally adjust an endoscopic instrument.

Laparoscopic, endoscopic, and other minimally invasive surgical techniques enable surgeons to perform fairly complicated procedures through relatively small entry points in the body. The term "laparoscopic" refers to surgical procedures performed on the interior of the abdomen, while the term "endoscopic" refers more generally to procedures performed in any portion of the body. Endoscopic surgery involves the use of an endoscope, which is an instrument permitting the visual inspection and magnification of a body cavity. The endoscope is inserted into a body cavity through a cannula extending through a hole in the soft tissue protecting the body cavity. The hole is made with a trocar, which includes a cutting instrument slidably and removably disposed within a trocar cannula. After forming the hole, the cutting instrument can be withdrawn from the trocar cannula. A surgeon can then perform diagnostic and/or therapeutic procedures at the surgical site with the aid of specialized medical instruments adapted to fit through the trocar cannula. Additional trocar cannulas may provide openings into the desired body cavity.

Some known advantages of minimally invasive surgical techniques include reduced trauma to the patient, reduced likelihood of infection at the surgical site, and lower overall medical costs. Accordingly, minimally invasive surgical techniques are being applied to an increasingly wider array of medical procedures.

FIG. 1 depicts a typical example of an endoscopic instrument 100. The instrument 100 may include a handle 110, a knob 120, and a tubular member 130. The handle 110 may be one of a variety of conventional configurations, such as a grip handle shown in FIG. 1. A portion of the handle 110 fits within a proximal end of the knob 120, providing an axis about which the knob 120 can be rotated. A distal end of the knob 120 may engage the proximal end of the tubular member 130, such that any rotation of the knob 120 may cause the tubular member 130 to rotate as well. The distal end of the tubular member 130 may include one of a variety of instruments or so-called end effectors. For example, the distal end may be equipped with jaws, cutting blades, or some other instrument, depending on the desired use of the endoscopic instrument.

It is often useful for a practitioner of endoscopic surgery to rotationally manipulate the distal end of the tubular member 130 while firmly grasping the handle 110 in a comfortable manner, thus allowing the distal end of the tubular member to rotate relative to the handle. Additionally, it is often useful to incrementally rotate the distal end of the tubular member 130 by some predetermined angular displacement so that the practitioner may visualize the rotation relative to the handle 110.

FIG. 2 depicts a cross section of a knob 120 having a conventional ball and spring detent mechanism. Within the knob 120 is a cylindrical drum 205 having a plurality of detents 210. Typically, a channel 215 may extend partially through the knob 120, the channel 215 being oriented radially with respect to the cylindrical drum 205. The ball and spring mechanism is positioned within the channel 215.

As the name implies, a compression spring 220 is used to hold a ball 225 in contact with the cylindrical drum 205. To prevent the ball and spring mechanism from falling out of the knob 120, a set screw 230 may be used to seal the channel 215. The set screw 230 may also be used to adjust the amount of compression force that is applied to the spring 220. The ball, spring, and set screw may be separate components or may be integrated into a single component, as is known to the art. The portion of the handle that fits within the knob may engage the cylindrical drum 205, or the cylindrical drum 205 may be an integral part of the handle.

As the knob 120 is rotated with respect to the handle, the ball 225 travels around the circumference of the cylindrical drum 205. When the ball 225 is aligned opposite to one of the detents 210, the spring 220 pushes the ball 225 into the detent 210. If additional rotational force is applied to the knob 120, then the ball 225 is removed from the detent 210. The amount of force needed to remove the ball 225 from the detent 210 depends on a number of factors, including the shape and depth of the detent 210, the shape and size of the ball 225, and the amount of compression force applied by the spring 220 and/or set screw 230. The spring 220 is conventionally made of metal to provide sufficient compressive force. The movement of the ball 225 into and out of the detents 210 provides tactile feedback to the user.

While the ball and spring detent mechanism design approach is functional, it requires several components and assembly processes to assure instrument reliability. Even so, these devices often fail over time as the metal components corrode causing the mechanism to jam.

Accordingly, there is a need to provide an incremental rotational displacement mechanism for use with endoscopic instruments that is resistant to corrosion failure and that may be easily assembled.

SUMMARY

In accordance with the present invention, there is an endoscopic instrument having a circular detent housing coupled to a first end of a knob. The circular detent housing has a plurality of detents arranged along the perimeter of the detent housing. A tubular member fixedly engages a second end of the knob. A detent ring is positioned coplanar to and within the perimeter of the detent housing. The detent ring has at least one detent arm and at least a portion of the at least one detent arm engages at least a portion of the detent housing. A handle is coupled to the detent ring.

In accordance with another aspect of the invention, there is an incremental rotational displacement mechanism. The mechanism includes a circular detent housing, a detent ring, and a handle. The detent housing has a plurality of detents arranged along the circumference of the detent housing. The detent ring has at least one detent arm and is positioned coplanar to and within the circumference of the detent housing, such that at least a portion of the at least one detent arm engages at least a portion of the detent housing. The handle engaging the detent ring such that a force applied to the handle causes the detent ring to rotate with respect to the circular detent housing.

In accordance with yet another aspect of the invention, the circular detent housing is formed within the first end of the knob.

In accordance with still another aspect of the invention, the detent ring has at least two arms. The two arms may have the same length or have different lengths.

In accordance with another aspect of the invention, the plurality of detents are arranged at either regular or irregular intervals along the perimeter of the detent housing.

It should be emphasized that the term "comprises" or "comprising," when used in this specification, is taken to specify the presence of stated features, integers, steps, or components, but does not preclude the presence or addition of one or more other features, integers, steps, components, or groups thereof

BRIEF DESCRIPTION OF DRAWINGS

The objects and advantages of the invention will be understood by reading the following detailed description in conjunction with the drawings in which.

DETAILED DESCRIPTION

The present invention improves upon the state of the art by providing a more reliable incremental rotational displacement mechanism for use with endoscopic instruments. Furthermore, the mechanism may be implemented using fewer components.

Figure 1:
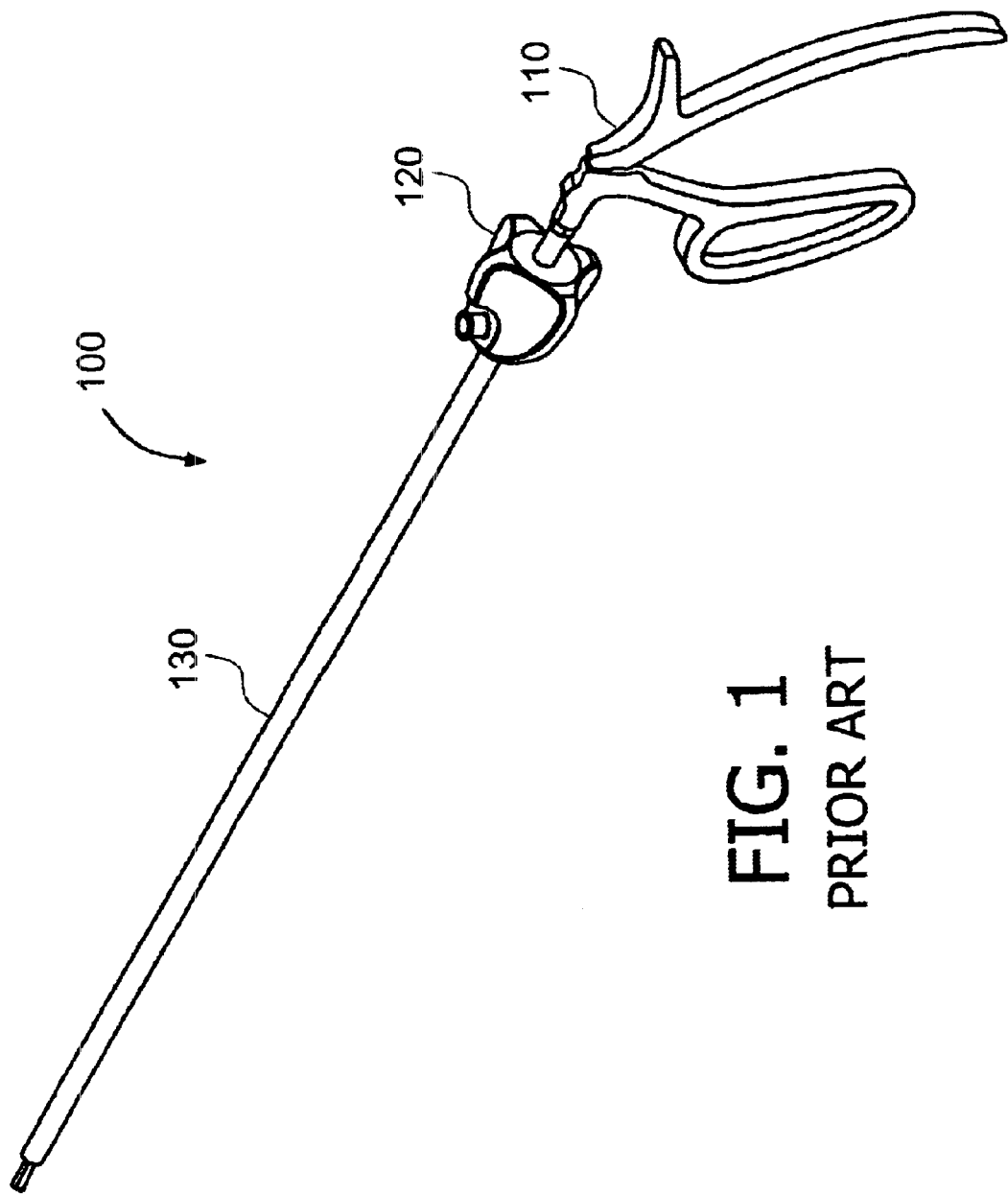
FIG. 1 is a plan view of an endoscopic instrument.
Figure 3:
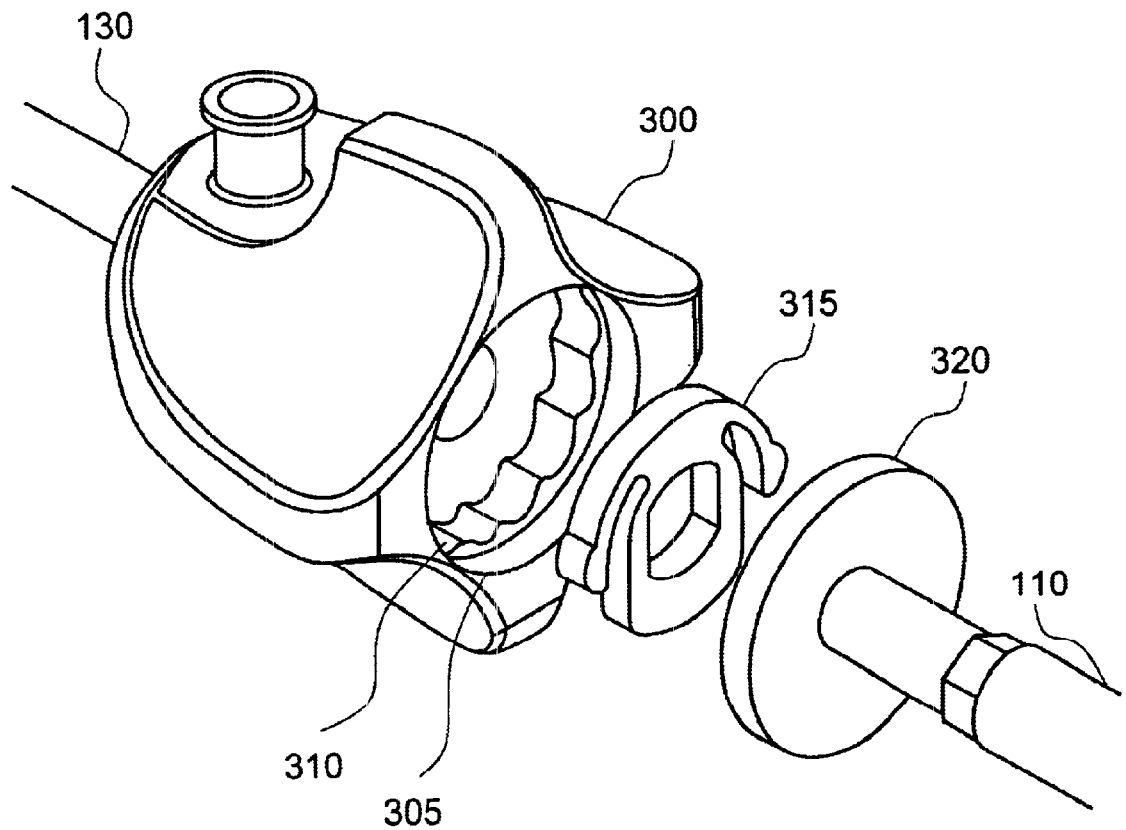
FIG. 3 is an exploded view of the knob of an endoscopic instrument showing an exemplary embodiment of a detent mechanism in accordance the invention.

FIG. 3 is an exploded view of a knob 300 of an endoscopic instrument showing an exemplary embodiment of an incremental rotational displacement mechanism in accordance with the invention. It will be appreciated that the knob 300 shown in FIG. 3 replaces the knob 120 shown in FIG. 1. Thus, from the perspective of the user, each of the knobs 300, 120 performs an equivalent function.

A cylindrical cavity 305 is formed in a proximal end of the knob 300. Arranged around the circumference of the cavity 305 are a plurality of scalloped detents 310. A detent ring 315 may be disposed at least partially within the cavity 305 and in the same plane as the cavity 305. A knob plug 320 may be disposed at least partially within the cavity 305 and positioned proximally to the detent ring 315. The knob plug 320 provides a mechanical seal for the cavity 305 and retains the detent ring 315 in place. As discussed below, the shaft portion of the handle 110 mates with a center hole of the detent ring 315, thereby rotationally fixing the detent ring to the shaft portion 110 of the handle.

Figure 4:
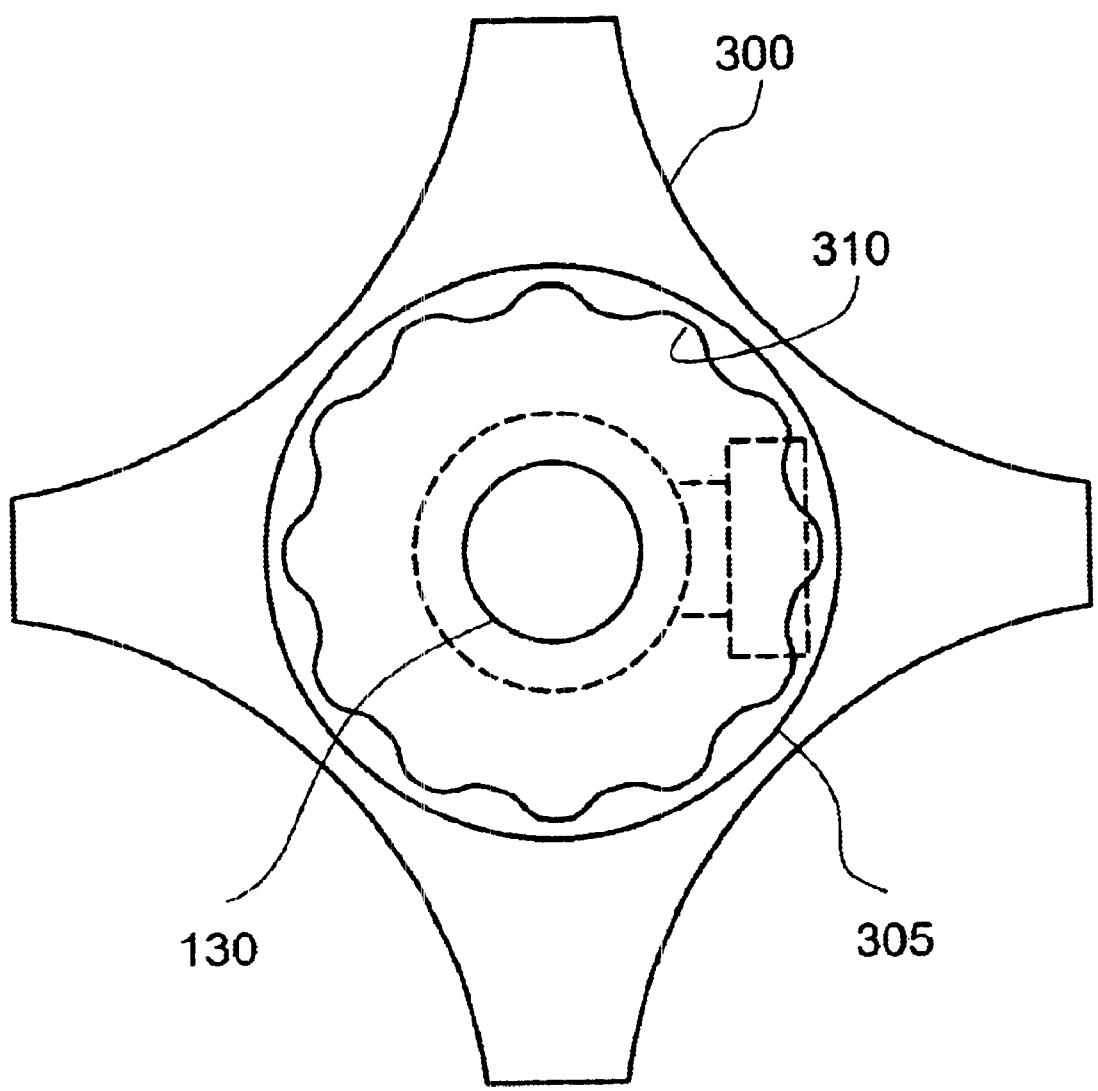
FIG. 4 is a plan view of the proximal end of the knob.

FIG. 4 shows a plan view of the knob 300 showing the cylindrical cavity 305 and the plurality of scalloped detents 310. The knob 300 may be formed from a variety of materials, such as polymers and metals, using conventional techniques. For example, the knob may be formed by injection molding an acetal resin, such as Delrin® 150 available from E.I. du Pont de Nemours and Company. If the knob 300 is injection molded, then the knob 300, the cylindrical cavity 305, and the plurality of scalloped detents 310 maybe formed from a single process step.

As can be appreciated, the number of detents 310 and the distance between each of the detents 310 may determine the angular resolution of the incremental rotational displacement mechanism. In one embodiment, twelve detents 310 are equally spaced around the perimeter of the cavity 305, resulting in a granularity of about 30 degrees of angular resolution. The number of detents may be increased or decreased to provide a greater or lesser amount of angular resolution. In addition, detents may be absent from portions of the perimeter of the cavity, creating "dead zones".

Figure 2:
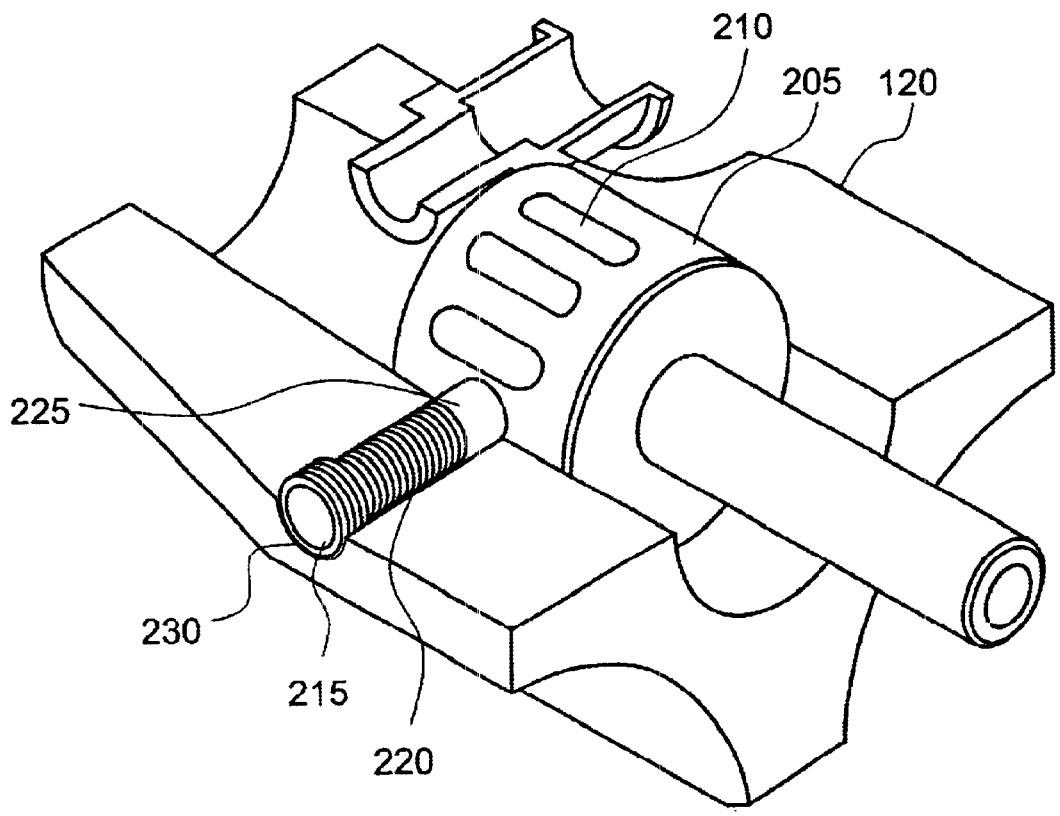
FIG. 2 is a partial cross-section of the knob of an endoscopic instrument having a conventional ball and spring detent mechanism.
Figure 5A:
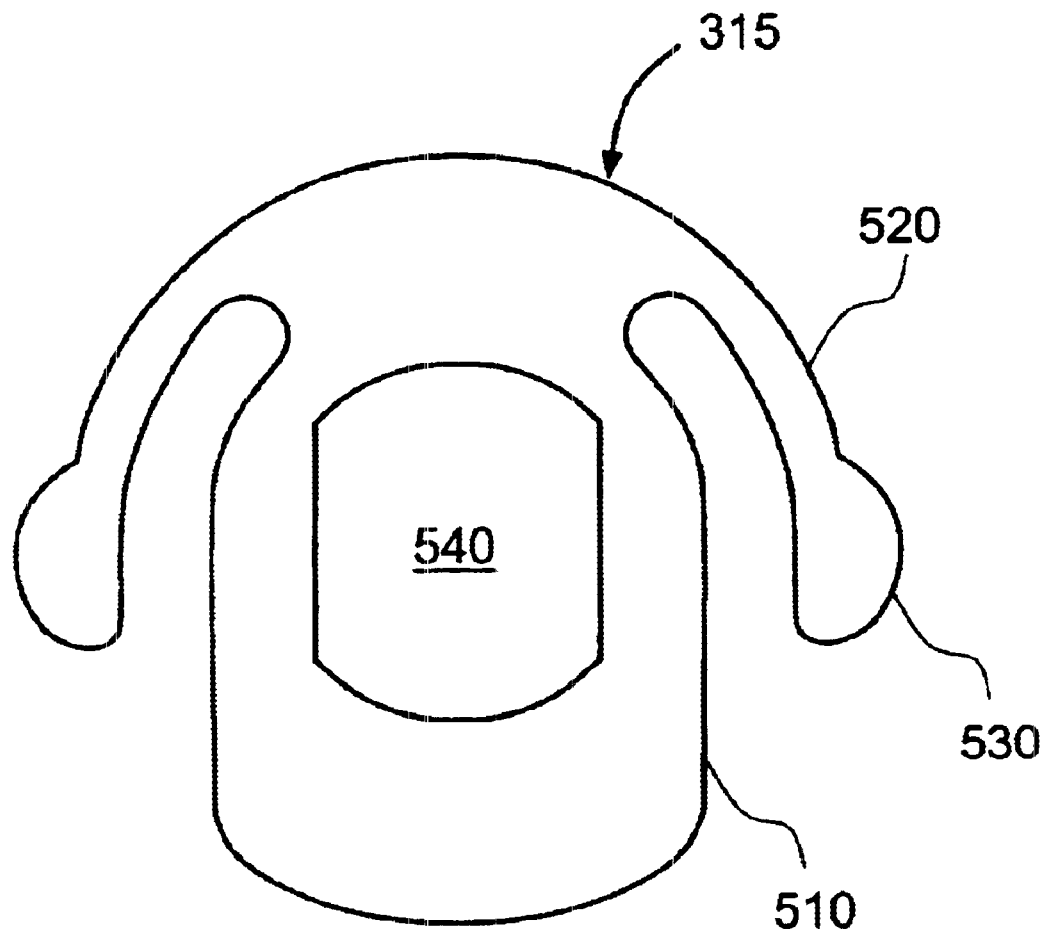
FIGS. 5a and 5b are a plan views of two embodiments of the detent ring.
Figure 5B:
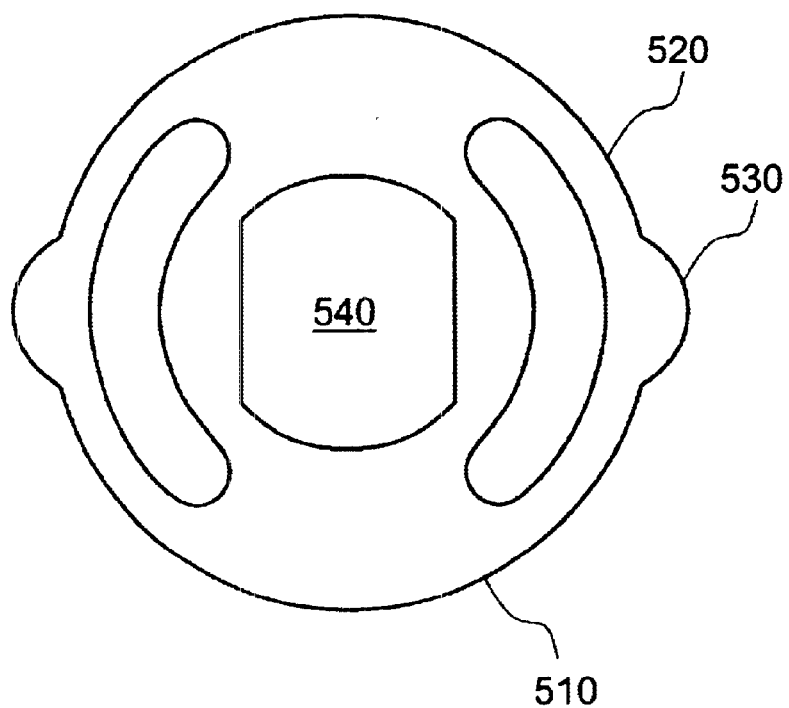

FIG. 5a shows a plan view of the detent ring 315. The detent ring may include a main body 510 and at least one arm 520. One end of the arm 520 may be connected to the main body 510 and the other end of the arm may terminate in a tab 530. In another embodiment, shown in FIG. 5b, the arm 520 may extend from one end of the main body 510 to another end of the main body 510, with the tab 530 located along the length of the arm. In either case, the tab 530 may be shaped to engage the scalloped detents. The tab 530 and at least one arm 520 are arranged such that the tab 530 moves in and out of the detents 310 as the detent ring 315 is rotated within the cavity 305. As the tab 530 moves in and out of the detents 310, the user experiences some tactile feedback, similar to that felt with the conventional ball and spring mechanism shown in FIG. 2.

As mentioned above, an opening 540 may extend through the center of the main body 510. The opening 540 may have at least one flat portion. The shaft of the handle may be "keyed" to the shape of the opening 540, so that when the shaft is inserted into the opening, the shaft and the detent ring may be rotationally fixed.

The material used to make the detent ring 315 should be compatible with that material used to make the knob 300. Factors used to determine compatibility may include chemical interaction. In addition, the material should be chosen to minimize any burring or wear of either the detent ring 315 or the detents 310 after repeated used. The detent ring 315 may be formed using similar materials and techniques used to form the knob 300. For example, the detent ring 315 may be formed by injection molding an acetal resin, such as the previously described Delrin® 150.

The amount of force needed to rotate the knob 300 can be varied by changing the characteristics of the detent ring 315. For example, the thickness of at least one arm 540 can be increased or decreased to provide a greater or lesser amount of resistance to movement with respect to the main body 510. In addition, the composition of the material used to make the detent ring 315 can be changed. For example, other polymers could be mixed with or substituted for the acetal resin used to make the detent ring 315. In addition, metal or alloys could be used to form all or part of the detent ring 315. Examples of other suitable materials include stainless steel or nickel titanium alloys, such as nitinol.

Figure 6C:
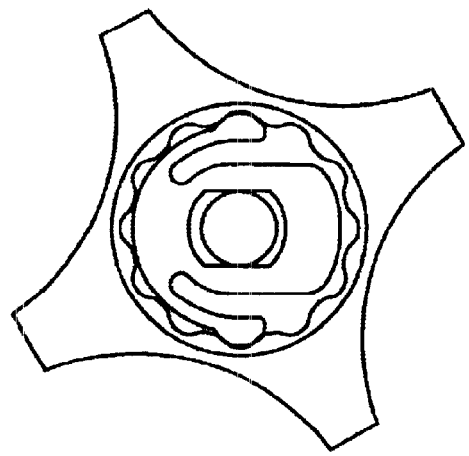
FIGS. 6a, 6b, and 6c are sequence drawings of a knob rotation.
Figure 6B:
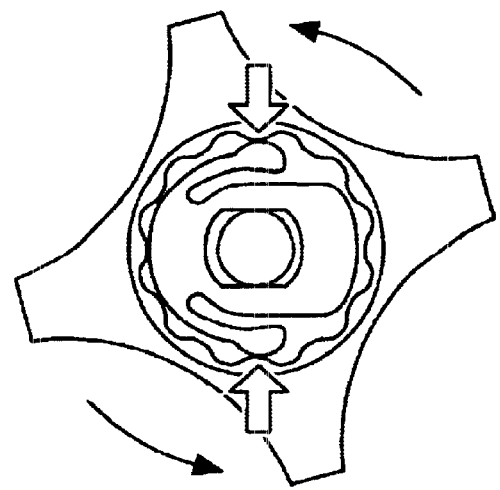
Figure 6A:
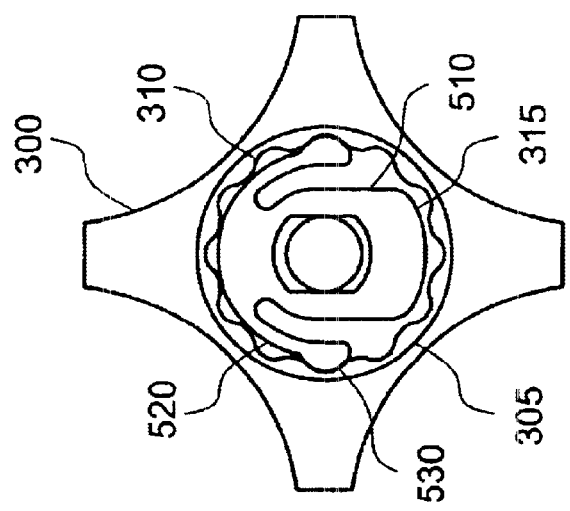

FIG. 6a shows the detent ring 315 positioned within the cylindrical cavity 305 of the knob 300. The shaft of the handle 110 and the knob plug 320 are not shown. In FIG. 6a, the tabs 530 fully engage the detents 310. As shown in FIG. 6b, the knob 300 maybe rotated counter-clockwise with respect to the detent ring 315, as indicated by the arrow 601. As the knob 300 is rotated, a portion of the detents 310 assert a radial force against the tab 530 portions of the arms 520, pushing the arms 520 toward the main body 510 portion of the detent ring 315. This is indicated by the arrows 602, 603 in FIG. 6b. The knob 300 may continue to be rotated counter-clockwise until the tabs 530 fully engage another pair of detents 310, as shown in FIG. 6c. As can be appreciated, while FIGS. 6a, 6b, and 6c show the knob 300 being rotated counter-clockwise, the knob 300 may also be rotated clockwise. Due to the symmetrical shape of the tab 530, the detent ring 315 interacts with the detents 310 in the same manner regardless of which direction the knob 300 is rotated.

Figure 7:
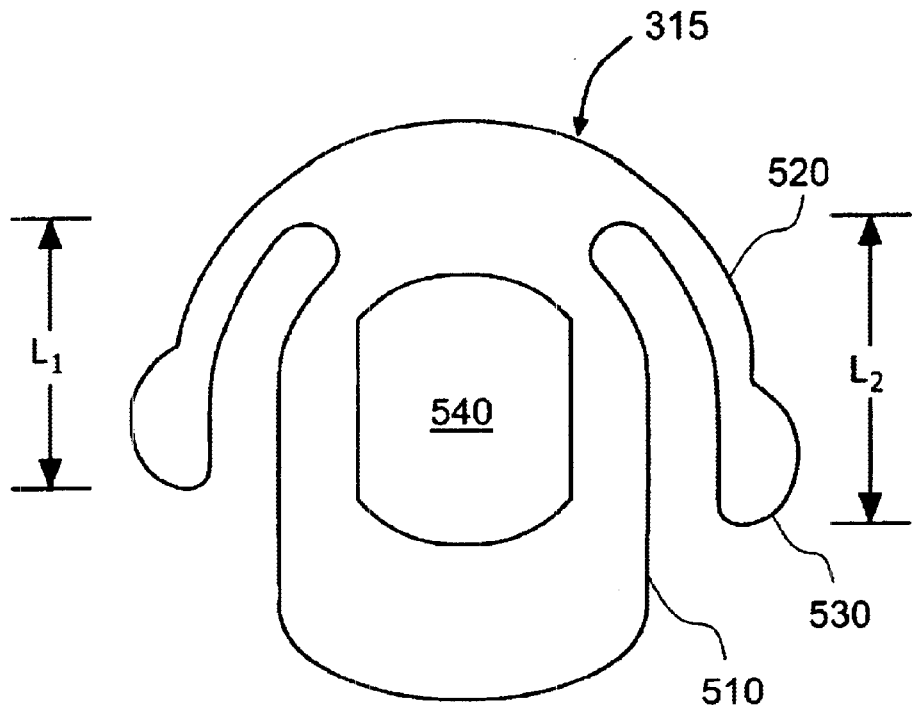
FIG. 7 is a plan view of another embodiment of the detent ring.

As noted above, the number of detents 310 and the distance between each of the detents 310 may determine the angular resolution of the incremental rotational displacement mechanism. The angular resolution of the incremental rotational displacement mechanism may also be determined by the length of the arms of the detent ring. For example, FIG. 7 depicts an embodiment of the detent ring 315 having arms of unequal lengths. A first arm may have length $L_1$ and a second arm may have length $L_2$, where $L_2$ is greater than $L_1$. As can be appreciated, one tab 530 may be engaged in a detent while the other tab is situated somewhere between two adjacent detents and is thus disengaged. As the knob 300 is rotated, the engaged tab may become disengaged from its detent and the previously disengaged tab may become engaged in another detent. Thus, the effective angular rotation of the incremental rotational displacement mechanism may be somewhere between the angular distance between two adjacent detents.

The invention has now been described with respect to several embodiments. In light of this disclosure, those skilled in the art will likely make alternate embodiments of this invention. These and other alternate embodiments are intended to fall within the scope of the claims which follow.

What is claimed is:

1. An endoscopic instrument comprising:
   a knob having a first end and a second end;
   a circular detent housing coupled to the first end of the knob, the circular detent housing having a plurality of detents arranged along an inside circumference of the detent housing;
   a tubular member fixedly coupled to the second end of the knob;
   a detent ring having at least one detent arm, the detent ring being positioned coplanar to and within the inside circumference of the detent housing, wherein at least a portion of the at least one detent arm engages at least one of the plurality of detents; and
   a handle fixedly coupled to the detent ring.

2. The instrument of claim 1, wherein the circular detent housing is formed within the first end of the knob.

3. The instrument of claim 1, wherein the detent ring has at least two arms.

4. The instrument of claim 3, wherein the detent ring has two arms having the same length.

5. The instrument of claim 3, wherein the detent ring has two arms having different lengths.

6. The instrument of claim 1, wherein the plurality of detents are arranged at regular intervals along the inside circumference of the detent housing.

7. The instrument of claim 1, wherein the plurality of detents are arranged at irregular intervals along the inside circumference of the detent housing.

8. The instrument of claim 1, further comprising a knob plug disposed within the first end of the knob between the handle and the detent ring.

9. An incremental rotational displacement mechanism comprising:
   a circular detent housing having a plurality of detents arranged along a circumference of the detent housing;
   a detent ring having at least one detent arm, the detent ring being positioned coplanar to and within the circumference of the detent housing, wherein at least a portion of the at least one detent arm engages at least a portion of the detent housing; and
   a handle engaging the detent ring whereby a force applied to the handle causes the detent ring to rotate with respect to the circular detent housing.

10. The mechanism of claim 9, wherein the detent ring has at least two arms.

11. The mechanism of claim 10, wherein the detent ring has two arms having the same length.

12. The mechanism of claim 10, wherein the detent ring has two arms having different lengths.

13. The mechanism of claim 9, wherein the plurality of detents are arranged at regular intervals along the circumference of the detent housing.

14. The mechanism of claim 9, wherein the plurality of detents are arranged at irregular intervals along the circumference of the detent housing.

* * * * *